United States Patent
Dalton et al.

(10) Patent No.: US 6,454,800 B2
(45) Date of Patent: Sep. 24, 2002

(54) CORNEAL ONLAY

(75) Inventors: Beatrice Ann Dalton, Narrabeen; John Gerard Steele, North Rocks; Margaret Diana Macrea Evans, Chatswood; Janet Helen Fitton, Tasmania; Graham Johnson, Peakhurst, all of (AU); Ilene Kay Gipson, Concord, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/782,346

(22) Filed: Feb. 12, 2001

Related U.S. Application Data

(63) Continuation of application No. PCT/EP99/05836, filed on Aug. 10, 1999.

(30) Foreign Application Priority Data

Aug. 12, 1998  (EP) .............................. 98115161

(51) Int. Cl.⁷ .................................................. A61F 2/14
(52) U.S. Cl. ..................................................... 623/5.11
(58) Field of Search .............................. 623/5.11, 5.13, 623/5.14, 5.15

(56) References Cited

U.S. PATENT DOCUMENTS

| 4,449,257 | A |   | 5/1984 | Koeniger |
| 4,902,292 | A |   | 2/1990 | Joseph |
| 5,123,921 | A | * | 6/1992 | Werblin et al. ............. 623/5.11 |
| 6,090,141 | A | * | 7/2000 | Lindstrom ................. 623/5.11 |
| 2001/0018612 | A1 | * | 8/2001 | Carson et al. ............. 623/5.11 |

FOREIGN PATENT DOCUMENTS

| EP | 0 162 573 A | 11/1985 |
| FR | 2 661 816 A | 11/1991 |

* cited by examiner

Primary Examiner—Dinh X. Nguyen
(74) Attorney, Agent, or Firm—R. Scott Meece; Rob Gorman; Richard Gearhart

(57) ABSTRACT

A corneal onlay or corneal implant is disclosed which is to be placed within or onto the surface of the cornea, being a biocompatible, optically transparent, synthetic and biostable polymeric material, said material comprising a surface that supports the attachment and growth of tissue cells, and where the exterior surface of the implant onto which epithelial tissue is to be attracted and to become attached, or in the case of a corneal onlay the anterior surface of the onlay, has a topography comprising a plurality of surface indentations.

11 Claims, No Drawings

CORNEAL ONLAY

This application is a continuation of International Application No. PCT/EP99/05836, filed Aug. 10 1999, the contents of which are incorporated by reference.

This invention is directed to an improved corneal onlay. More specifically the corneal onlay of the invention has a surface topography and a structure of the anterior surface which promote overgrowth with corneal epithelium and formation of a stratified epithelium following overgrowth, including the development of hemidesmosomes in basal cell layer of the epithelium.

The invention is particularly directed towards an implant for use for synthetic epikeratoplasty or as an implanted contact lens, where placed at an subepithelial site.

The objective of the invention is to provide a polymer surface that inherently supports tissue overgrowth without the need for an additional surface modification or biological coating. A further objective is to provide a polymer that combines this property with good biostability, optical properties, and mechanical properties that make the material suitable for the fabrication of epikeratoprostheses.

Corneal onlays as such are known. One of the more recent findings, as disclosed in EP-A-729323, suggests that a corneal onlay needs to be porous to allow for through passage between anterior and posterior sides of the device of trophic factors and nutrients. Said EP-A-729323 is illustrative for a number of reasons, it is explaining the background state of the art, and definitions used therein do apply also to this invention, unless terms are expressly otherwise defined. A number of synthetic polymers have been proposed for a corneal onlay, or other corneal implant where epithelialisation is desired, such as hydrophobic materials, for example perfluoropolyether based materials, or collagen-hydrogel copolymeric materials.

However, the prior art examples do not teach, nor make predictable, the requirements as to the topography of the surface of a synthetic polymer for
(i) the processes of the migration of corneal epithelial tissue across the surface of an implant;
(ii) the processes of the assembly of a stratified corneal epithelium following movement of the tissue across the surface of the material. In considering this migration process, it needs to be recognized that there is a difference between the ocular epitzhelium and other epithelia for cellular migratory processes. In the case of the corneal epithelium, the epithelial cells that are found in the central region of the cornea arise initially from stem cells that lie in the limbal region (the zone that is the transition between the conjunctiva and the cornea). That is, there is a movement of epithelial cells from the limbal region to the central cornea. This compares with the situation of other epithelia, where the stem cells lie in the lower levels of the epidermis and cellular movement preceding, during, or to permit, stratification is towards the anterior surface;
(iii) the processes of the formation of hemidesmosomes (at the basal epithelial cells) at and into the near surface of the synthetic material;
other than to show that a topography that is supportive is possible.

The disadvantages of the prior art corneal onlays are overcome by the corneal onlay of this invention based on the surprising finding that for migration of the corneal epithelium to cover the onlay, it is not the pores which are relevant but a topography comprising a plurality of indentations.

The corneal onlay or corneal implant to be placed within or onto the surface of the cornea according to the disclosure herein has a surface topography in order to permit the overgrowth of a surface of the implant with corneal epithelium. The corneal epithelium tissue overlying the corneal onlay device shows characteristics of being a stratified corneal epithelium, including the presence in the basal epithelial cell layer of proteinaceous components of hemidesmosome structures.

The present invention is distinct from the prior art in that it arises from the recognition that the topography of the surface, independent of the porosity of the material, can promote the overgrowth of a corneal onlay with corneal epithelial tissue.

The invention provides a polymer surface for use in a corneal onlay, which surface has a topography that supports the overgrowth and migration of corneal epithelial tissue at a level that is superior to that seen for a smooth and non-porous form of the same synthetic polymer.

A further distinguishing feature from the prior art is that the surface according to the current invention combines this topography, with porosity.

The invention is therefore directed to a corneal onlay or corneal implant to be placed within or onto the surface of the cornea, being a biocompatible, optically transparent, synthetic and biostable polymeric material, said material comprising a surface that supports the attachment and growth of tissue cells, and where the exterior surface of the implant onto which epithelial tissue is to be attracted and to become attached, or in the case of a corneal onlay the anterior surface of the onlay, has a topography comprising a plurality of surface indentations.

A surface that supports the attachment and growth of tissue cells either provides said support directly, or said surface additionally has a surface coating that supports the attachment and growth of tissue cells.

It is important to note that the surface indentations may comprise pores, but pores alone are not within the meaning of surface indentation. In other words, the wording "topography comprising a plurality of surface indentations" includes surfaces having pores plus indentations, but excludes surfaces having pores without additional indentations. Apart from the fact that corneal onlays having pores, and no indentations, as disclosed in EP-A-729323, are not within the scope of the present invention, the indentations may have any suitable form and geometry.

Preferred characteristics of the plurality of indentations are that they are equal or greater than 500 square nanometers in surface area and equal or less than 0.7 square microns in surface area in the plane of the surface, or that they are generally curvilinear or circular in shape at the plane of the surface and have minimum diameter(s) that is/are equal or greater than 0.025 microns in diameter and have maximum diameter(s) that is/are equal or less than 0.95 microns in diameter.

More preferred minimum diameters are equal or greater than 0.05 microns in diameter.

More preferred maximum diameters are equal or less than 0.80 microns in diameter, even more preferred equal or less than 0.50 microns in diameter and most preferred equal or less than 0.35 microns in diameter.

Another set of preferred features of the plurality of surface indentations is that they comprise the equivalent area in the plane of the surface as to be equal or greater than 0.10 % of the surface area in the plane of the surface and equal or less than 20% of the surface area. More preferred values in this context are that the surface indentations comprise the equivalent area in the plane of the surface as to be equal or greater than 2% of the surface area in the plane of the surface and equal or less than 15% of the surface area in the plane of the surface, and most preferred is a range from equal or greater than 3% of the surface area in the plane of the surface and equal or less than 10% of the surface area in the plane of the surface.

It may be appropriate to make a comment on terminology used herein: Some of the sizes of the indentations mentioned hereinbefore refer to the size of individual indentations, and there are a plurality of indentations of these sizes. Such indentations may not all be identical in size but would generally fit these size ranges. Sizes of this type are for example those referred to in claims 2 and 3. In contrast thereto, some of the sizes specified hereinbefore are for the totality of the indentations in aggregate. Sizes of this type are for example those referred to in claim 4. It is believed that the person skilled in the art will understand this differentiation taking into account the absolute magnitude disclosed.

It is also preferred that the mean depth of surface indentations below the plane of the surface is equal or greater than 0.1 microns.

It is further preferred that the surface indentations do not provide for the ingrowth of corneal epithelial tissue or cells or cellular processes to a depth of further than 20 microns from the plane of the surface of the implant, or more preferred the surface indentations do not provide for the ingrowth of corneal epithelial tissue or cells or cellular processes to a depth of further than 20 microns from the plane of the surface of the implant in the optical region of the implant.

The surface indentations as described hereinbefore may or may not have a coating or gel formed of biological molecules or synthetic analogues thereof placed upon or within said plurality of surface indentations.

A gel as mentioned hereinbefore may be made, for example, from collagen which is or is not chemically crosslinked to the surface and wherein the collagen molecules within the gel are crosslinked or uncrosslinked.

Furthermore, some or aH of the plurality of surface indentations as disclosed hereinbefore may have continuity with other indentations within the bulk of the material below the plane of the surface.

Also, the existence of pores, in addition to surface indentations, through the implant or onlay is possible. In such a case the pores are preferably curvilinear or circular and the diameter of the pores is in the range of equal or greater than 0.025 microns in diameter and equal or less than 0.95 microns in diameter. More preferred values in this context are 0.05 microns in diameter and equal or less than 0.35 microns in diameter.

A preferred corneal onlay has the following characteristics: It combines the elements of claims 1 to 3, 1 to 4, 1 to 5, 1 to 6, or 8 and 10 and 11. Other combinations of preferred features of the invention are also possible and within the scope of this invention. This statement includes aspects of the invention disclosed hereinbefore and such aspects following hereinafter.

Further preferred aspects of the invention are in that the topography of the anterior surface of the onlay comprises indentations as defined hereinbefore and pores as defined hereinbefore and that said topography consists of a plurality of surface indentations that are equal or less than 10.000 square nanometers in surface area.

Another preferred aspect of the invention is in that the topography of the anterior surface of the onlay comprises indentations as defined hereinbefore and pores as defined hereinbefore and that said topography consists of a plurality of surface indentations which have a maximum diameter that is equal or less than 0.4 microns in diameter. More preferably said maximum diameter ie equal or less than 0.2 microns in diameter.

The disclosure of the invention hereinbefore has been made particularly with reference to intraepithelial corneal onlays and other corneal implant materials. However, this fact should not be understood as being limiting in any substantial way. A material that supports the overgrowth of epithelial tissue may also have applications as a component of other intra-epithelial implants, such as percutaneous access devices.

The following examples are for illustration purposes only and are by no means intended to restrict the scope of the claims.

EXAMPLE 1

This example demonstrates that a material with a surface that contains a plurality of surface indentations provides for enhanced outgrowth of corneal epithelium, as compared to the same composition of material but a form which does not contain surface indentations. The demonstration was conducted in a cell culture assay where the ability of the material surface to support the overgrowth of corneal epithelial tissue is measured. This assay format therefore duplicates the situation of a corneal onlay device, in terms of the requirement that the surface of a corneal onlay promote the ability of the corneal epithelium to migrate over and cover the surface of the material.

Methods: Assembly of the materials for use in the assay using the Boyden chamber: The materials to be tested were assembled in modified "Boyden" chambers which have a structure such that the upper and lower chambers are separated by 25 mm diameter discs of the materials to be tested. These modified Boyden chambers consist of a base and upper section, which screw together above and below the material to be used in the culture assay. The polycarbonate base (5 cm square and 3.8 cm high) contains an inner semi-spherical lower chamber of 2 ml capacity. This lower chamber is connected to the exterior by 2 channels set on opposite sides of the chamber, which permit the diffusion of air such that the medium in the lower well can be buffered by the 5% $CO_2$ in air atmosphere within a cell culture incubator. At the top of the lower section and extending into the lower chamber, there is a 2 mm wide flat circular ledge that supports the peripheral 2 mms of the 25 mm diameter sample of material to be tested. The base contains a thread, onto which screws the upper section, manufactured from polytetrafluoroethylene. Between the lower and upper sections and supported by the ledge, are placed the material sample to be tested which can be either a single sheet, or alternatively two sheets of material. If there are two sheets of materials, these sheets will be held in very tight apposition by the pressure exerted by the thread mechanism. A silicone gasket with an internal diameter of 23 mm and an external diameter of 25 mm is placed between the material sample and the upper section, to enable a fluid-tight seal to be formed and culture medium is introduced into both the lower and upper chambers. The lower sections of the Boyden chamber were completely filled with medium (approx. 2 ml) and 1.5 ml of medium was added to the upper sections.

Description of materials tested: Track-etched polycarbonate membranes (free from wetting agents, from Poretics Corporation, USA; 0.4 microns nominal pore diameter). These membrane materials contained columnar pores with measured diameters of 0.35 microns. Control materials (that is, Sample A) used in the assays were non-porous polycarbonate.

Corneal epithelial tissue overgrowth assay: Corneas were excised from freshly enucleated bovine eyes and the bulk of the stromal tissue and the endothelial layer were removed. A skin biopsy punch was used to collect six mm diameter buttons of corneal tissue from the periphery of the tissue. Explants so collected comprised an intact epithelium with a small amount of stromal tissue attached but greater than 90% of the stromal tissue had been removed. The explants were placed (stromal side down) on the material surfaces and were covered with Dulbecco's modified Eagle's medium/Ham's F12 (ICN Flow) supplemented with 5 microgram/ml insulin, 5 microgram/ml transferrin, 5 nanogram/ml selenious acid (from Collaborative Research) 60 microgram/ml penicillin and 100 microgram/ml streptomycin (ICN Flow). The cultures were maintained at 37° C. in an humidified atmosphere containing 5% $CO_2$ in air (v/v) for a period of nine days, with changes of medium at day three and day six. After this period, the explants were washed with phosphate buffered saline (PBS) and fixed in 10% (v/v) formalin in PBS for 30 min at room temperature, washed with distilled water and air dried for 5 minutes. The explants were stained with 0.1% (w/v) Crystal violet (Edward Gurr Ltd) in 0.02 M phosphate buffer (pH 7) for 30 minutes at room temperature then washed 3 times with distilled water to remove any unbound stain. The total area of the tissue (epithelial outgrowth+original area of explant button) was measured by image analysis (Quantimet 570, Leica Cambridge). An index of epithelial tissue outgrowth (Tissue Outgrowth Index) was calculated by dividing the final surface area of the outgrowth from each explant by the initial area of the tissue explant. Therefore, a Tissue Outgrowth Index value of 1.0 represents a situation where there was no outgrowth of corneal epithelial tissue onto the surface. Each experiment was repeated twice and four replicates were set up for each treatment.

Results: The extent of corneal epithelial tissue overgrowth was compared for three different polycarbonate materials:

Sample A: a smooth, nonporous polycarbonate surface.

Sample B: a surface made from the same material but with a plurality of surface indentations of 0.35 micron measured diameter on the material; the plurality of surface indentations comprise the equivalent area in the plane of the surface as to be 9% of the surface area in the plane of the surface. This sample was provided by a 0.4 micron nominal diameter track-etched pore polycarbonate membrane. In Sample B this material was assembled in tight apposition to a non-porous material on the underside and therefore no flux of proteins or fluids was permitted through the upper membrane material.

Sample C: a surface with a plurality of surface indentations on the material, and having in addition pores that enabled a flux of fluids and proteins and nutrients through the membrane material.

The extent of corneal epithelial tissue overgrowth onto these samples during a nine day culture period was measured as:

|  | Sample | | |
| --- | --- | --- | --- |
|  | A | B | C |
| Tissue Outgrowth Index value | 4.9 +/− 0.6 | 10.1 +/− 0.8 | 9.0 +/− 0.8 |

When subjected to the Student-Newman-Keuls Multiple Comparisons statistical test, the following conclusion was made: Samples B and C showed a statistically significantly higher value for the Tissue Outgrowth Index than Sample A (both at the level of $P<0.05$) but there was no statistically significant difference between Sample B and Sample C ($P>0.05$).

This experiment shows that for a material that supported the overgrowth of corneal epithelial tissue onto a generally smooth surface (Tissue Outgrowth Index greater than 1 for Sample A), this material when in the form of a surface with a plurality of indentations of 0.4 microns nominal diameter and 0.12 square microns in surface area in the plane of the surface supported a significantly superior extent of outgrowth of corneal epithelial tissue (Samples B and C). This superior level of corneal epithelial tissue outgrowth was also seen for the case of when the material enabled the flux of fluid and proteins and nutrients through the pores of the material but was not dependent upon this fluid or molecular movement, as it was also seen for the case where the pores at the surface of the material could not support such a flux of fluid and proteins and nutrients.

EXAMPLE 2

This experiment showed that for a series of materials with the same surface chemistries as to the chemical composition of the synthetic polymer surface, the material that has a plurality of indentations supported a significantly superior extent of outgrowth of corneal epithelial tissue than the equivalent smooth surface. This was seen for both a synthetic polymer surface and also for materials which had covalently attached collagen on the surface. In these materials the plurality of indentations in the surface were of 0.075 microns nominal diameter and 7850 square nanometers in surface area in the plane of the surface. The plurality of surface indentations and pores comprised the equivalent area in the plane of the surface as to be 2.5% of the surface area in the plane of the surface.

EXAMPLE 3

In this example, the role of polymer surface topography in the assembly of basement membrane and hemidesmosomes (which together are known to be responsible for the persistent adhesion of the stratified epithelium to its underlying stroma in intact cornea) by epithelial cells at the tissue-material interface was tested. Each hemidesmosome is comprised by keratin intermediate filaments and hemidesmosomal plaque on the posterior aspect of the basal epithelial cells, which link through the basement membrane to anchoring fibrils that penetrate the anterior stroma, thereby securing the epithelium to its connective tissue.

Methods and Materials:

Sample A: as described in Example 1 above.

Sample C: a surface made from the same polycarbonate material but with a plurality of surface indentations of 0.35 micron measured diameter on the material ("value A" in following table), and having in addition pores that enabled a flux of fluids and proteins and nutrients through the membrane material. This sample was provided by a 0.4 micron nominal diameter track-etched pore polycarbonate membrane ("value B" in following table). The plurality of surface indentations and pores comprise the equivalent area in the plane of the surface as to be 9% of the surface area in the plane of the surface ("value C" in following table).

Samples D, E and F are the same as Sample C, with the exception that the Values A, B and C are modified as evident from the following Table

| Sample | Value A | Value B | Value C |
|--------|---------|---------|---------|
| C | 0.35 micron | 0.4 micron | 9% |
| D | 0.075 micron | 0.1 micron | 2.5% |
| E | 0.72 micron | 0.8 micron | 10.7% |
| F | 0.9 micron | 1 micron | 10% |

Buttons of explanted corneal tissue were placed on triplicate samples of each surface and maintained in culture for 21 days, during which time epithelial tissue outgrew in direct contact with the underlying polymer. Ultrathin sections of the epithelial tissue-polymer interface were examined using transmission electron microscopy and the formation along the interface of basement membrane and hemidesmosomal plaque (identified from ultramicroscopic features) was recorded.

Results: Cells constituting the basal layer of epithelial cells on the Sample A material (a smooth and non-porous polycarbonate surface) lay in close apposition to the polymer surface and there was little or no evidence of basement membrane along this tissue-polymer interface, and no evidence of hemidesmosomal plaque components.

Cells in contact with the surface containing a plurality of indentations of 0.075 microns diameter (Sample D) consistently bridged these pore openings. With the surface indentations of this size, there was a continuous basement membrane formation and a regular pattern of hemidesmosomal plaque assembly even across the indentation. Cells in contact with the surfaces containing a plurality of indentations of 0.4, 0.8 or 1 microns nominal diameters (Samples C, E and F) effectively bridged the pores, although cell cytoplasm was observed to protrude slightly into the mouth of some surface indentations. In contrast to the membranes with the surface containing a plurality of indentations of 0.075 microns diameter, however, the formation of basement membrane and hemidesmosomal plaque on each of these surfaces lacked continuity and was restricted to those regions where the solid portion of the polymer (between the pores) was immediately subjacent to the cells. That is, the surface indentations interrupted the continuity of the basement membrane and assembly of hemidesmosomal plaque, when the surface indentations were of a size of 0.4 microns and greater in diameter.

This work shows that the assembly of structures responsible for persistent epithelial adhesion (including a continuous basement membrane and hemidesmosomal plaque, as is seen at the epithelial-stromal interface in intact corneal tissue) are supported on a surface that contains indentations of no greater than 0.4 microns diameter for a material that contains porosity towards tissue factors and nutrients.

What is claimed is:

1. A corneal onlay or corneal implant to be placed within or onto the surface of the cornea, being a biocompatible, optically transparent, synthetic and biostable polymeric material, said material comprising a surface that supports the attachment and growth of tissue cells, and where the exterior surface of the implant onto which epithelial tissue is to be attracted and to become attached, or in the case of a corneal onlay the anterior surface of the onlay, has a topography comprising a plurality of surface indentations.

2. An onlay or implant according to claim 1, wherein the plurality of indentations are equal or greater than 500 square nanometers in surface area and equal or less than 0.7 square microns in surface area in the plane of the surface.

3. An onlay or implant according to claim 1, wherein the plurality of indentations are generally curvilinear or circular in shape at the plane of the surface and have minimum diameter(s) that is/are equal or greater than 0.025 microns in diameter and have maximum diameter(s) that is/are equal or less than 0.95 microns in diameter.

4. An onlay or implant according to claim 1, wherein the plurality of indentations comprise the equivalent area in the plane of the surface as to be equal or greater than 0.10% of the surface area in the plane of the surface and equal or less than 20% of the surface area.

5. An onlay or implant according to claim 1, wherein the mean depth of surface indentations below the plane of the surface is equal or greater than 0.1 microns.

6. An onlay or implant according to claim 1 wherein the plurality of indentations do not provide for the ingrowth of corneal epithelial tissue or cells or cellular processes to a depth of further than 20 microns from the plane of the surface of the implant.

7. An onlay or implant according to claim 1, wherein in that the plurality of indentations have a coating or gel formed of biological molecules or synthetic analogues thereof placed upon or within said plurality of surface indentations.

8. An onlay or implant according to claim 1, wherein it comprises pores through the implant or onlay.

9. An onlay or implant according to claim 8, wherein the pores are curvilinear or circular and the diameter of the pores is in the range of equal or greater than 0.025 microns in diameter and equal or less than 0.95 microns in diameter.

10. An onlay or implant according to claim 8, wherein the plurality of indentations are equal or less than 10.000 square nanometers in surface area.

11. An onlay or implant according to claim 8, wherein the plurality of indentations have a maximum diameter that is equal or less than 0.4 microns in diameter.

* * * * *